United States Patent [19]

Brännström et al.

[11] Patent Number: 4,588,763

[45] Date of Patent: May 13, 1986

[54] ETHYL ACETATE AS SOLVENT IN CAVITY LINERS

[76] Inventors: Martin Brännström, Lagårdsvägen 7, Saltsjö-Duvnäs, Sweden, S-130 11; Hans Wahlstam, Dalkärrsleden 110, Vällingby, Sweden, S-162 24

[21] Appl. No.: 911,480

[22] Filed: Jun. 1, 1978

[51] Int. Cl.[4] .................. C08L 93/00; A61C 5/00
[52] U.S. Cl. .................... 524/77; 433/217.1
[58] Field of Search ............ 32/15; 260/31.2, 27 R; 524/77; 433/217

[56] References Cited

U.S. PATENT DOCUMENTS 4,046,732  9/1977  Infantee .................. 260/31.2 R

FOREIGN PATENT DOCUMENTS 2122028  1/1971  France ...................... 32/15
870322  6/1961  United Kingdom .............. 32/1

Primary Examiner—Joseph L. Schofer
Assistant Examiner—Peter F. Kulkosky
Attorney, Agent, or Firm—Cushman, Darby & Cushman

[57] ABSTRACT

Ethyl acetate is used as solvent for polymers in dental cavity liner compositions.

5 Claims, No Drawings

ETHYL ACETATE AS SOLVENT IN CAVITY LINERS

BACKGROUND OF THE INVENTION

When the dentist is restoring a tooth, the cavity made is cleaned and thereafter insulated. As insulation so called "cavity liners" are used. These cavity liners have been thick and cement-like. They present many inconveniences, such as e.g. the fact that they cannot be applied but to the floor of the cavity. Since they do not cover the important sidewalls, they do not reduce the risk of secondary caries. Furthermore, they are voluminous and can gradually be entirely dissolved. Some of them even irritate the pulp.

It is also known that varnish, e.g. a vehicle together with a solvent, has been tried as insulation agent. The insulation obtained has not proved to be completely satisfactory, particularly not as to bacterial invasion. Furthermore, there will be a space between the cavity walls and the insulation, which moreover does not prevent growth of existing bacteria.

Recently cavity liners have been used consisting of a resin dissolved in chloroform together with a suspension of some other substances, particularly salts. The resin employed has especially been polystyrene and the suspended substance employed has been $Ca(OH)_2$ and/or ZnO. In other types of cavity liners calciummonofluorophosphate and diiodide dithymol have been used. Such cavity liners have proved to provide a good protection to most filling materials, particularly if they have been applied under specified conditions, in which case, however, certain clinical difficulties exist.

The principal object of the insulation is to protect against growth of bacteria in the space between the filling and the cavity wall and to prevent bacterial invasion from the oral cavity and to prevent toxins from diffusing through the dentinal tubules to the pulp. The following requirements should therefore be put on a liner:

it should not be tissue irritating;

it must be easy to apply the means of an air-blast to a thin and uniform film (thickness about 3–10 $\mu$m), which well covers the whole surface of the cavity;

only one application should be sufficient for achieving a satisfactory protection;

a good adaptation should take place to ground dentinal and enamel surfaces which have been cleaned and dried with an air blast (with a remaining monolayer of fluid);

it should have bacteriostatic properties;

it should protect against bacterial invasion in the space between filling and cavity wall; in other words, the liner should be of such a nature that it, when absorbing fluid, (especially from the dentin, where tissue fluid exists and all the time provides pressure from the inner of the tooth) expands so that a contraction space of about 1–10 $\mu$m as far as possible is filled by the liner, said contraction space being the result of the hardening of the filling material, and that it is not dissolved to any greater extent by oral liquids and acids, which can be formed in bacterial plaques in connection with the outer limit of the filling;

it should not be appreciably influenced by a short contact with 30–50% by weight phosphoric acid, followed by water flushing.

It has been proved that salts, which are found in the prior known liner, should be part of the suspension. A smaller amount of $Ca(OH)_2$ in a thin plastic film does not apparently bring about any detectable positive effect as to dentin. The same applies to smaller amounts of fluoro containing salts.

Thus, in prior known cavity liners chloroform is used as a solvent for the resinous materials (plastic materials) used, which can be polystyrene, polyacrylate and similar resins, for instance. However, it has now been known that chloroform as a solvent presents a number of inconveniences. Thus, it is now suspected to have cancerogenic properties. Furthermore, it is poisonous.

THE INVENTION

According to the invention ethyl acetate is used as the solvent for the resins in cavity liners, where it replaces the chloroform.

It has been shown that ethyl acetate can very well completely replace chloroform as a good solvent for the resins (plastic materials) contained in cavity liners, particularly such resins of polystyrene type. It also provides a rapid evaporation. Ethyl acetate has no unpleasant taste or smell. It is nonpoisonous in small quantities, such as those used in cavity liners. The toxicity cannot be doubted either, since it is a naturally occurring flavouring substance in most fruits, as e.g. in oranges, apples and pears.

The invention is in more detail explained in the following examples.

EXAMPLE 1

| | |
|---|---|
| Zinc oxide | 5.0 g |
| Calcium hydroxide | 5.0 g |
| Calciummonofluorophosphate dihydrate | 2.0 g |
| Diiodide dithymol | 1.0 g |
| Polystyrene | 4.0 g |
| Ethyl acetate | q.s. 100 ml |

The polystyrene and the diiodide dithymol are solved in about 80 ml ethyl acetate, whereafter the inorganic salts are added. The dispersion obtained is thereafter poured into bottles during a continuous stirring in order to make the dispersion uniformly distributed.

EXAMPLE 2

| | |
|---|---|
| Zinc oxide | 5.0 g |
| Calcium oxide | 5.0 g |
| Calciummonofluorophosphate dihydrate | 2.0 g |
| Irgasan DP 300 | 0.2 g |
| Polystyrene | 4.0 g |
| Ethyl acetate | q.s. 100 ml |

EXAMPLE 3

| | |
|---|---|
| Zinc oxide | 5.0 g |
| Calcium hydroxide | 5.0 g |
| Irgasan DP 300 | 0.2 g |
| Polystyrene | 4.0 g |
| Rosin | 0.4 g |
| Ethyl acetate | q.s. 100 ml |

EXAMPLE 4

| | |
|---|---|
| Zinc oxide | 5.0 g |
| Calcium oxide | 2.5 g |

-continued

| | |
|---|---|
| Diiodide dithymol | 1.0 g |
| Cellulose acetate | 10.0 g |
| Polyvinyl acetate | 2.0 g |
| Canada balsam | 0.1 g |
| Ethyl acetate/ethanol 80/20 | q.s. 100 ml |

EXAMPLE 5

| | |
|---|---|
| Zinc oxide | 5.0 g |
| Calcium hydroxide | 5.0 g |
| Diiodide dithymol | 1.0 g |
| Collodion | 8.0 g |
| Polyvinyl acrylate or polyvinyl acetate | 5.0 g |
| Ethyl acetate | q.s. 100 ml |

EXAMPLE 6

| | |
|---|---|
| Zinc oxide | 5.0 g |
| Calcium hydroxide | 5.0 g |
| Diiodide dithymol | 1.0 g |
| Methylmethacrylate | 4.0 g |
| Polystyrene | 3.0 g |
| Ethyl acetate | q.s. 100 ml |

This invention is thus concerned with cavity liners having ethyl acetate as solvent instead of chloroform, the other ingredients of the cavity liners being unchanged.

It has been shown that the addition of zinc oxide and particularly calcium oxide in liners of the invention promotes the adhesion of the liner to the exposed dentin surface of the cavity, probably by its dehydrating effect. The amount of the oxide, especially that of calcium, is normally in the range of 1-10 g per 100 ml cavity liner of the invention.

Furthermore, it has been shown that the addition of a non-toxic, natural balsam, as e.g. Copaiba and Canada balsam, provides a liner that due to its expanding and elastic properties gives a reduced contraction space which may occur between the filling material and liner. The amount of balsam should preferably be 0.1-1 g per 100 ml cavity liner of the invention.

The resinous material to be used in the cavity liners of the invention is preferably a polyacrylate or polymethacrylate and most preferred polystyrene. A mixture of resinous materials can be used.

The amount of resinous material to be used in the cavity liner of the invention depends on its nature and is not critical. It is easy to establish a suitable amount by simple experiments, so that the viscosity and other properties of the liner will be such that the liner thickness on the cavity walls will be in the desired range, as e.g. 5-50 $\mu$m. The amount can be 1-20 g, preferably 2-10 g, per 100 ml cavity liner.

What is claimed is:

1. A dental cavity liner composition comprising a resin selected from the group consisting of polystyrene, polyacrylate, polymethacrylate and mixtures thereof, a non-toxic balsam, and a solvent consisting of ethyl acetate.

2. The composition of claim 1 wherein calcium oxide is included in the cavity liner composition.

3. The composition of claim 1, wherein said resin is polystyrene.

4. The composition of claim 1, wherein said resin is selected from the group consisting of polyacrylate and polymethacrylate.

5. A cavity liner which consists essentially of
   (a) 1-10 grams per ml of cavity liner of zinc oxide, calcium oxide and mixtures thereof;
   (b) 9.1-1 gram per 100 ml of cavity liner of a non-toxic natural balsam;
   (c) 1-20 grams per 100 ml of cavity liner of a resin selected from polystyrene, polyacrylate, polymethacrylate and mixtures thereof; and
   (d) q.s. 100 ml of ethyl acetate.

* * * * *